(12) United States Patent
Schmitt

(10) Patent No.: US 7,105,180 B2
(45) Date of Patent: Sep. 12, 2006

(54) STABLE GALENIC PREPARATIONS COMPRISING A BENZIMIDAZOLE AND METHOD FOR THE PRODUCTION THEREOF

(75) Inventor: Benoit Schmitt, Irvine, CA (US)

(73) Assignee: Ratiopharm GmbH, Ulm (DE)

(*) Notice: Subject to any disclaimer, the term of this patent is extended or adjusted under 35 U.S.C. 154(b) by 520 days.

(21) Appl. No.: 10/149,068

(22) PCT Filed: Dec. 6, 2000

(86) PCT No.: PCT/EP00/12286

§ 371 (c)(1),
(2), (4) Date: Aug. 26, 2002

(87) PCT Pub. No.: WO01/41734

PCT Pub. Date: Jun. 14, 2001

(65) Prior Publication Data

US 2003/0114494 A1   Jun. 19, 2003

(30) Foreign Application Priority Data

Dec. 9, 1999   (DE)   ............................. 199 59 419

(51) Int. Cl.
*A61K 9/24* (2006.01)
*A61K 9/28* (2006.01)

(52) U.S. Cl. .................... 424/472; 424/471; 424/482; 514/772; 514/772.2

(58) Field of Classification Search ................ 424/468, 424/475, 479, 480, 482; 514/772
See application file for complete search history.

(56) References Cited

U.S. PATENT DOCUMENTS

| 3,712,886 A | | 1/1973 | Koyanagi et al. | |
| 4,370,313 A | | 1/1983 | Davies | |
| 4,786,505 A | * | 11/1988 | Lovgren et al. | ............ 424/468 |
| 5,232,706 A | | 8/1993 | Palomo Coll | |
| 5,626,875 A | * | 5/1997 | Ballester Rodes et al. | .. 424/464 |

FOREIGN PATENT DOCUMENTS

| DE | 31 51 196 A1 | 12/1981 |
| DE | 32 33 764 A1 | 9/1982 |
| EP | 0 005 129 A1 | 10/1979 |
| EP | 0 122 815 | 10/1984 |
| EP | 0 124 495 A2 | 11/1984 |
| EP | 0 237 200 A3 | 9/1987 |
| EP | 0 244 380 A3 | 11/1987 |
| EP | 0 247 983 A2 | 12/1987 |
| EP | 0 342 522 A1 | 11/1989 |
| EP | 0 519 144 A * | 6/1991 |
| EP | 0 773 025 A1 | 5/1997 |
| EP | 0 519 144 B1 | 8/1997 |
| GB | 1190387 | 5/1970 |
| GB | 1 589 982 | 5/1981 |
| GB | 0646006 | 3/1997 |
| JP | 58-109413 | 6/1983 |
| JP | 59-20219 | 2/1984 |
| JP | 9132522 | 9/1996 |
| PT | 101826 | 2/1996 |
| WO | WO 92/22284 | 12/1992 |
| WO | WO 93/25204 | 12/1993 |
| WO | WO 96/37195 | 11/1996 |
| WO | WO 98/19668 | 5/1998 |
| WO | WO 98/40069 | 9/1998 |
| WO | WO 98/52564 | 11/1998 |
| WO | WO 99/48498 | 9/1999 |
| ZA | 74/3391 | 5/1974 |

OTHER PUBLICATIONS

"Introduction of Our Four Excipients", *Technical Bulletin*Shin-Etsu Chemical Co., Ltd. (1975).
"Hydropoxypropyl Methylcellulose TC-5", Shin-Etsu Chemical Co., Ltd., 1-15 (1975).
Lee, JC, "Cellulose Acetate Phthalate", *Handbook of Pharmaceutical Excipients*, 2nd Edition, 91-93 (1994).
Shek, E. et al., "Cellulose Acetate Phthalate", *Handbook of Pharmaceutical Excipients*, 51-52 (1986).
Monaco, A.L. et al., "Hydropoxypropyl Methylcellulose Phthalate", *Handbook of Pharmaceutical Excipients*, 141-144 (1986).
Holstills, E.A. et al., "Polymethacrylates", *Handbook of Pharmaceutical Excipients*, 214-216 (1986).
Ellis, J.R. et al., "Chapter 12-Tablet Coating", *The Theory and Practice of Industrial Pharmacy*, 2nd Edition, 359-386 (1976).
"The National Formulary—16th Edition", *The United States Pharmacopeia*, 21st Revision, 1242-1246 (1985).
Lieberman et al., "Sugar-Coating Techniques", *Pharmaceutical Dosage Forms*, vol. 3, 85-87 (1982).
Stachura, J. et al., *Hepato-gastroenterol.*, 30, 205-210 (1983).
Lind et al., *Gut*, 24, 270-276 (1983).
Shukla, AJ, "Polymethacrylates", *Handbook of Pharmaceutical Excipients*, 2nd Edition, 362-366 (1994).
Rackur, G. et al., *Biochemical and Biophysical Research Communications*, 128(1), 477-485 (1985).

(Continued)

Primary Examiner—Michael G. Hartley
Assistant Examiner—Micah-Paul Young
(74) Attorney, Agent, or Firm—Reed Smith, LLP

(57) ABSTRACT

The invention relates to a novel benzimidazole formulation and to a process for its production. The benzimidazole formulation comprises a layer comprising the benzimidazole compound together with an acidic reacting compound.

20 Claims, No Drawings

OTHER PUBLICATIONS

Tsuda, et al. "Basic Course of Drug Development XI", *The Production of Pharmaceuticals*, vol. 1, 1-57 (1971)—English Translation.

Pilbrant, A. et al., *Scandinavian Journal of Gastroenterology*, 20(108), 113-120 (1985).

"Introduction and Uses of TC-5", *Hydroxypropyl Methulcellulose TC-5*, 1-3 (1975).

Kubo, et al., Japan Industrial Technology Federation, "Coating of Drugs", *Up-to-date Pharmaceutical Technology Series*, No. 1, 1-3 (1969).

International Search Report, PCT/EP 00/12286, Dec. 6, 2000.

Schepky, "Stabilisierung von physikalischen Eigenschaften fester Arzneiformen", *Stabilisierungstechnologie Wege zur haltbaren Arzneiform*, 45-64 (1986).

Bauer, "Übersicht uber Inkompatibilitatsmoglichkeiten, insbesondere bei der Umhullung von Arzneizubereitungen", *Deutsche Apotheker Zeitung*, 118(4) 125-130 (1978).

Klotz, U., "Klinische Pharmakologie von 5-Aminosalicylsaure", *Therapie chronisch entzundlicher Darmerkrankungen*, 221-227 (1985).

Dechesne et al., Ubersetzung von Auszugen aus *J. Pharm.*, Belg., 37(4), 273-282 (1982).

Lehmann et al., "Anwendung waBriger Kunststoffdispersionen zum Uberziehen von Arzneiformen", *Pharm. Ind.*, 34(11a), 894-899 (1972).

"Qualitatsnormen und Analysenmethoden fur Eudragit L 30 D", *Röhm Pharma.*, (1982).

Bauer et al., "Studien uber waBrige Applikationsformen einiger synthetischer Polymere fur dunndarmlosliche Filmuberzuge" *Pharm. Ind.*, 41(12), 1203-1207 (1979).

Voight et al., *Lehrbach der pharmazeutischen Technologie*, 218 ( Verlag Chemie, 1979).

Lehmann et al., *Praktikum des Lack-Dragierens*, 1-13 (Rohm Pharma 1983).

Bauer et al., "Kombatibilitat und Stabilitat", *Pharmazeutische Technologie*, 571-593 (1986).

List et al., *Hagers Handbuch der Pharmazeutischen Praxis*, 760 (1971).

Hengels, "Omeprazol: Wirkungen und Nebenwirkungen" *Z. Gastroenterologie*, 22, 241-243 (1984).

Greenwood N.N., Earnshaw A., *Chemistry of the Elements*, Department of Inorganic and Structural Chemistry, University of Leeds, U.K., pp. 598-599 (Pergamon Press, 1984).

* cited by examiner

STABLE GALENIC PREPARATIONS COMPRISING A BENZIMIDAZOLE AND METHOD FOR THE PRODUCTION THEREOF

The application claims priority to DE 19959419, filed Dec. 09, 1999 and PCT/EP00/23386, filed Dec. 6, 2000.

FIELD OF THE INVENTION

The invention relates to a novel pharmaceutical formulation of a benzimidazole, in particular of omeprazole or of a similar compound, which is stable although it contains no alkaline reacting compound but, on the contrary, an acidic reacting compound in contact with the benzimidazole. The invention also relates to a process for the production of such a formulation.

BACKGROUND OF THE INVENTION

It is generally assumed that benzimidazoles such as omeprazole are unstable in an acidic environment and that, for this reason, pharmaceutical formulations comprising such a benzimidazole ought to comprise an alkaline reacting compound. One example of such a formulation is described in EP-A 0 247 983.

It is possible by combining the benzimidazoles with a sufficient quantity of alkaline reacting compound to obtain pharmaceutical formulations having quite good stability. However, pharmaceutical formulations of this type have intrinsic problems. For example, acidic groups are present in the enteric coating of the formulations and are able to react with the alkaline reacting compound of the core. Whereas it is well known to separate the alkaline reacting core from the enteric coating by an intermediate layer, great care must be applied during the production of such pharmaceutical formulations in order to adjust the thickness and nature of the intermediate layer and the nature of the enteric coating to the alkalinity of the core so that a pharmaceutical formulation with adequate stability and good bioavailability is obtained. Problems of this type are discussed, for example, in example 1 of EP-A 0 247 983.

Some formulations in which the benzimidazole is not combined with an alkaline reacting compound have recently been developed. One example of such a development is described in U.S. Pat. No. 5,626,875, corresponding to EP-A 0 773 025. This publication discloses a formulation comprising
  an inert core,
  which is coated with a first layer which comprises the benzimidazole together with a water-soluble polymer,
  a further layer comprising a water-soluble polymer and an enteric coating.

In the examples of this publication, the benzimidazole is formulated with excipients which are generally regarded as inert, such as, for example, talc. Talc in pharmaceutical quality may, however, contain impurities, and a pH of more than 7 is often measured in a suspension of talc in water (ISFET technique for phenol red indicator).

Several recently developed omeprazole-containing pharmaceuticals combine omeprazole with a specific stabilizer in order to increase the stability of the composition, such as, for example, mannitol (EP-A 646 006), $TiO_2$ (WO 96/37195) or cyclodextrins (WO 98/40069) or amino acids. However, it would be desirable to have available an omeprazole-containing pharmaceutical which is sufficiently stable without such a stabilizer.

There is a need for pharmaceuticals which comprise benzimidazole compounds and, in particular, omeprazole or a similar compound as active ingredient, which have an excellent stability combined with good bioavailability, and which do not show the problems and disadvantages of some prior art pharmaceuticals.

The present invention is based on the unexpected finding that the benzimidazoles which have been regarded as very acid-labile in fact have an excellent stability when they are formulated together with a compound which provides a pH of less than 7 if they are brought into contact with sufficient water in order to measure a pH (acidic reacting compound, acidic substance).

SUMMARY OF THE INVENTION

The invention thus provides a stable oral pharmaceutical which comprises a benzimidazole compound of the formula I

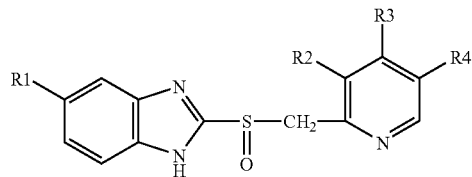

in which R1 is hydrogen, methoxy or difluoromethoxy, R2 is hydrogen, methyl or methoxy, R3 is methoxy, 2,2,2-trifluoroethoxy or 3-methoxypropoxy, and R4 is hydrogen, methyl or methoxy, comprising:
  (a) an inert core,
  (b) thereon an active ingredient layer which comprises the benzimidazole compound of the formula I mixed with an acidic reacting compound and, where appropriate, pharmaceutically acceptable adjuvants,
  (c) at least one inert layer and
  (d) an outer layer which is applied to the inert layer and which comprises an enteric coating.

The invention also provides a process for producing the pharmaceuticals of the invention, which comprises the following steps:
  (i) preparation of an inert core
  (ii) coating of the inert core with a benzimidazole layer,
  (iii) application of one or more inert layers
  (iv) application of the enteric coating.

DETAILED DESCRIPTION OF THE PREFERRED EMBODIMENTS

The benzimidazoles of the formula I are generally known as effective inhibitors of gastric acid secretion. Typical examples of such benzimidazole compounds are omeprazole, lanzoprazole and pantoprazole. Most preference is given to omeprazole.

The inert core is preferably a known sugar/starch. This inert core is coated with the benzimidazole layer. The benzimidazole layer comprises the active ingredient, the benzimidazole, in combination with the acidic reacting compound. Pharmaceutically acceptable excipients may likewise be present. The benzimidazole layer will generally comprise a water-soluble polymer (which is preferably non-alkaline) as binder, which is explained hereinafter.

The benzimidazole layer is coated with the inert coating which separates the first coating which comprises the benzimidazole, and the enteric coating. The inert coating generally comprises a water-soluble polymer and, where appropriate, other pharmaceutically acceptable excipients.

It is preferred for the pH of an aqueous suspension or solution obtained from the inert coating to be about 7. If two inert coatings are present, the pH of an aqueous suspension or solution of the first inert coating is preferably lower than the pH of an aqueous suspension or solution of the second inert coating.

It is preferred for at least two inert coatings (or layers; "layer" and "coating" is used synonymously in this description) to be present. The first inert coating generally comprises a water-soluble polymer, which is preferably non-alkaline, where appropriate an acidic reacting compound and, where appropriate, pharmaceutically acceptable excipients. The second inert coating, which is applied between the first inert coating and the enteric coating, generally comprises a water-soluble polymer, which is preferably non-alkaline, where appropriate an acidic reacting compound and, where appropriate, pharmaceutically acceptable excipients. The second inert coating and the first inert coating preferably have different compositions.

The first inert coating (if present) serves as barrier between the active benzimidazole layer and the second inert coating, which may comprise ingredients which ought not to come into contact with the benzimidazole layer. This first layer normally comprises a water-soluble polymer, preferably an acidic reacting compound and conventional excipients such as, for example, a lubricant. Polyethylene/polypropylene glycol, known as poloxamer, is preferred as lubricant.

The second inert layer serves as intermediate layer between the enteric coating and the inert part of the preparation. It normally comprises a water-soluble polymer and is ordinarily free of the acidic reacting compound (but may comprise the latter). It may furthermore comprise conventional excipients such as talc and pigments, for example titanium dioxide.

If only one inert layer is present, this inert layer ordinarily has the same composition as the second inert layer described above.

The enteric coating serves as conventional enteric coating. It comprises conventional enteric substances known in the prior art, such as cellulose phthalates and copolymers of the methacrylic acid type, for example methacrylic acid/alkyl (meth)acrylate copolymers, which are sold, for example, under the name Eudragit®. A methyl radical and an ethyl radical are preferred as alkyl radical.

The methacrylic acid type C copolymer complying with the US pharmacopeia is preferred. The product Eudragit L30D55 is particularly preferred. A preferred polymer is a copolymer based on methacrylic acid and ethyl acrylate. The formula is as follows:

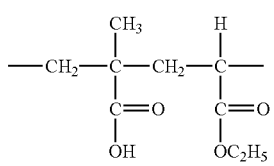

The ratio of free carboxyl groups to esters groups is preferably about 1:1. The average molecular weight is, for example, about 250,000.

A copolymer of this type will dissolve easily at pH values above 5.5 to form salts.

Triethyl citrate and/or polyethylene glycol or similar compounds can be used as plasticizers in the enteric coating. Talc may also be present. Other conventional excipients may also be present.

There are no special restrictions on the acidic reacting compound present in the pharmaceuticals of the present invention. The acidic reacting compound is defined by providing a pH of less than 7 when it is suspended or dissolved in water.

In particular, the aqueous mixture used for coating and comprising the benzimidazole and the acidic reacting compound ought to have a pH of less than 7, preferably a pH in the range from 6.5 to 6.95, more preferably in the range from 6.6 to 6.95.

Accordingly, the layer which comprises omeprazole and the acidic reacting compound ought to provide a pH of less than 7 when it is suspended in water. An amount of 5 to 50 mg of the layer material, suspended in 100 mg of water, ought preferably to provide a pH in the range from 6.5 to 6.95, preferably from 6.6 to 6.95. The pH measurements ought preferably to take place immediately after the layer material has been suspended in water. "Immediately" means in this connection within 30 minutes, preferably within 5 minutes, after the material has been added to the water. It may be advantageous for practical reasons to measure the pH in a solution or suspension comprising the inert core together with the benzimidazole-containing layer. If the measurement is carried out in the presence of the inert core, it is particularly important for the measurement to be carried out immediately (preferably as soon as possible) after the material has been placed in the water, in order to avoid the risk of core material dissolving and influencing the pH. In particular, the core ought not to be broken up, so that the core material dissolves as slowly as possible.

If the inert coating comprises the acidic reacting compound, the pH of a solution or suspension of the inert coating ought to be less than 7; 5 to 50 mg of the coating material, suspended or dissolved in 100 mg of water, ought preferably to provide a pH in the range from 6.5 to 6.95, more preferably in the range from 6.6 to 6.95.

It is immaterial how the pH is measured, with preference for the known ISFET technology using an ISFET electrode. Unless indicated otherwise, pH measurements referred to in this description were done using ISFET technology at a temperature of 25° C.

The acidic reacting compound is preferably sodium dihydrogen phosphate ($NaH_2PO_4$) with which the best results in relation to stability can be achieved. The amount of the acidic reacting compound is determined by the desired pH.

The acidic reacting compound is necessarily present in the layer which comprises the benzimidazole and is preferably present in the inert layer. If two inert layers are present (preferred embodiment), the acidic reacting compound is preferably present in the first inert layer, while it is preferably absent from the second inert layer.

The water-soluble polymer, which is generally present in the benzimidazole layer and in the inert layer(s), acts as a binder and may be any polymer known to be soluble in water or rapidly disintegrating in water. It is possible to use the same water-soluble polymer in all layers in which it is present, or to use different water-soluble polymers in different layers. Preferred water-soluble polymers are non-alkaline water-soluble polymers, and hydroxypropylmethylcellulose and hydroxypropylcellulose are particularly preferred.

Conventional pharmaceutically acceptable excipients known to the skilled worker may be present in any of the 5 layers of the pharmaceutical. These excipients preferably provide a pH of about 7 (for example 5 to 9) in aqueous solution or suspension. The nature and quantity of these excipients can easily be determined by a skilled worker on the basis of his general expert knowledge.

Unless otherwise stated, the excipients comprise conventional binders, plasticizers, colorants, pigments such as titanium dioxide, talc and other known excipients.

It is unnecessary with the present invention for the benzimidazole-containing layer to comprise a specific stabilizer for the benzimidazole as described for several prior art pharmaceuticals, such as mannitol (EP-A 646 006), $TiO_2$ (WO 96/37195) or cyclodextrins (WO 98/40069) or amino acids. On the contrary, the benzimidazole-containing layer preferably comprises only the benzimidazole, the binder and the acidic reacting compound.

The particularly preferred pharmaceutical of the present invention is a pellet formulation comprising
(a) an inert core which is a sugar/starch core,
(b) coated with a mixture of omeprazole, hydroxypropylmethylcellulose and sufficient sodium dihydrogen phosphate for 5 to 50 mg of the coating material, suspended or dissolved in 100 mg of water, to provide a pH in the range from 6.5 to 6.95, preferably 6.6 to 6.95,
(c) a first inert coating applied to the omeprazole-containing layer, where the first inert coating consists essentially of hydroxypropylmethylcellulose, polyethylene/polypropylene glycol and sufficient sodium dihydrogen phosphate for 5 to 50 mg of coating material in 100 mg of water to provide a pH in the range from 6.5 to 6.95, preferably in the range from 6.6 to 6.95,
(d) a second inert coating applied to the first inert coating, where the second inert coating consists essentially of hydroxypropylmethylcellulose, talc and titanium dioxide, and
(e) an outer layer applied to the second inert coating, consisting essentially of methacrylic acid/alkyl (meth) acrylate copolymer, triethyl citrate and talc.

It is likewise preferred for a pellet which has only the inert core and the benzimidazole-containing coating to provide a pH in the range from 6.6 to 6.95 when it is suspended in 4 μl of deionized water. If two or more inert layers are present, it is likewise preferred for a pellet which has only the inert core, the benzimidazole-containing coating and the first inert coating to provide a pH in the range from 6.6 to 6.95 when it is suspended in 4 μl of deionized water. It is in turn preferred for the pH measurement to be carried out immediately after the material has been added to the water in order to minimize a possible effect of the inert core (within 30 minutes, preferably within 5 minutes, after the material has been introduced into the water).

The pharmaceuticals of the present invention can be produced by known processes. The coating steps are preferably carried out in a fluidized bed coating apparatus. The pharmaceuticals of the present invention are in the form of pellets, and the final dosage form administered to the patient is a capsule comprising the pellets. An alternative possibility is also to compress the pellets to a tablet.

It is preferred for drying steps to be carried out between the coating steps, but this is not absolutely necessary. If a drying step is carried out, it is unnecessary to interrupt the fluidized bed process (that is to say the drying step can be carried out in the fluidized bed), but obviously the spraying must be stopped during the drying step. If a drying step is carried out, it lasts about 10 to 20 minutes.

The following examples illustrate the invention but are not restrictive.

EXAMPLE 1

A dispersion is prepared from 140 g of deionized water, 20 g of omeprazole and 15 g of hydroxypropylmethylcellulose. The pH of this dispersion is adjusted to a pH of 6.65 with an aqueous 0.5 M sodium dihydrogen phosphate solution. The pH is measured by an ISFET electrode. 140 g of neutral pellets are coated in a fluidized bed coating apparatus with the suspension prepared in this way.

A suspension for the inert coating is prepared by dispersing 125 g of deionized water, 3 g of titanium dioxide, 5 g of talc and 15 g of hydroxypropylmethyl-cellulose. The pellets with the omeprazole coating are coated with this suspension in a fluidized bed coating apparatus.

The pellets produced in this way are coated in a known manner with an enteric coating. The suspension of the enteric coating is prepared from 30 g of methacrylic acid copolymer type C (complying with US pharmacopeia), 12 g of talc, 4.5 g of triethyl citrate and 95.0 g of deionized water. A fluidized bed coating apparatus is again used.

The pellets obtained in this way are stable and provide excellent bioavailability.

EXAMPLE 2

Example 1 was repeated with the exception that the coating of the inert cores with the omeprazole-containing layer was followed firstly by the application of a first coating layer. A coating solution prepared from 5 g of hydroxypropylmethylcellulose, 1.0 g of poloxamer 188, 40 g of deionized water and aqueous 0.5 M sodium dihydrogen phosphate solution to adjust the pH to about 6.9 was used for this purpose. The coating is applied in a fluidized bed coating apparatus. The next inert coating (second inert coating) and the enteric coating are then applied to this first inert coating, using the same components, quantities and techniques as described in Example 1 above.

The pellets obtained in this way show a superior stability and excellent bioavailability.

Where it is stated in this application that (a quantity) of 5 to 50 mg of a coating or layer material in 100 mg of water provides a pH in a predefined range, this of course means that to comply with the feature it is sufficient for any quantity of material from the range from 5 to 50 mg to provide in 100 mg of water a pH in the defined range. Thus, to comply with this feature, it is sufficient for example if 5 mg of layer material in 100 mg of water provides a pH in the defined range, even if a different quantity of layer material, such as 10 mg of layer material (or 50 mg of layer material), in 100 mg of water provides a pH which is outside the defined range.

What is claimed is:
1. An oral pharmaceutical formulation comprising a benzimidazole compound of the formula I

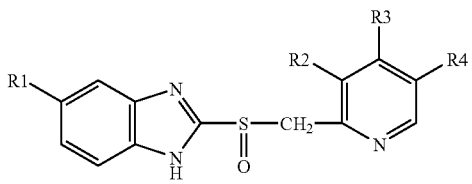

wherein R1 is hydrogen, methoxy or difluoromethoxy, R2 is hydrogen, methyl or methoxy, R3 is methoxy, 2,2,2-trifluoroethoxy or 3-methoxypropoxy, and R4 is hydrogen, methyl or methoxy, comprising
  (a) an inert core;
  (b) thereon, an active ingredient layer comprising the benzimidazole compound of the formula I mixed with an acidic reacting compound said active ingredient layer containing no alkaline reacting compound;
  (c) at least one inert layer; and
  (d) an outer layer, comprising an enteric coating, applied to the inert layer wherein an aqueous suspension of the active ingredient layer provides a pH of less than 7.

2. The pharmaceutical formulation of claim 1, wherein the active ingredient layer further comprises pharmaceutically acceptable adjuvants.

3. The pharmaceutical formulation of claim 1 having a first and second inert layer, wherein the first inert layer is applied to the active ingredient layer, and the second inert layer is applied to the first inert layer.

4. The pharmaceutical formulation of claim 3, wherein the first inert layer and the second inert layer comprise a water-soluble polymer.

5. The pharmaceutical formulation of claim 4, wherein the first inert layer and the second inert layer further comprise pharmaceutically acceptable excipients.

6. The pharmaceutical formulation of claim 4 or 5, wherein the first inert layer further comprises an acidic reacting compound.

7. The pharmaceutical formulation of claim 4, wherein the water-soluble polymer is at least one selected from the group consisting of hydroxypropylmethyl-cellulose and hydroxypropyl cellulose.

8. The pharmaceutical formulation of claim 6, wherein the acidic reacting compound comprises sodium dihydrogen phosphate.

9. The pharmaceutical formulation of claim 1, wherein the acidic reacting compound comprises sodium dihydrogen phosphate.

10. The pharmaceutical formulation of claim 1, wherein an aqueous suspension of the inert core and the active ingredient layer has a pH in the range from about 6.5 to 6.95, in particular from 6.6 to 6.95.

11. The pharmaceutical formulation of claim 1, wherein the benzimidazole compound of the formula I is omeprazole.

12. The pharmaceutical formulation of claim 1, wherein the formulation is in the form of pellets.

13. The pharmaceutical formulation of claim 12, wherein an aqueous suspension of the inert core and the active ingredient layer of a pellet in 4 μl of water has a pH in the range from about 6.5 to 6.95, in particular from 6.6 to 6.95.

14. The pharmaceutical formulation of claim 1, wherein the active ingredient layer and, if present, a first inert layer is free of talc.

15. The pharmaceutical formulation of claim 12, wherein the active ingredient layer consists essentially of omeprazole, hydroxypropylmethyl-cellulose and an acidic reacting compound which is present in an amount such that an aqueous suspension of the inert core with the active ingredient layer in 4 μl of water has a pH in the range from about 6.6 to 6.95;
  and having a first inert layer consisting essentially of hydroxypropylmethyl-cellulose, an acidic reacting compound and a lubricant;
  and a second inert layer consisting essentially of hydroxypropylmethyl-cellulose, talc and a pigment, in particular $TiO_2$;
  and wherein, the outer layer consists essentially of an enteric coating formed from methacrylic acid/alkyl (meth)acrylate copolymer, triethyl citrate and talc.

16. The pharmaceutical formulation of claim 15, wherein the acidic reacting compound is sodium dihydrogen phosphate.

17. A process for producing an oral pharmaceutical formulation of claim 1 comprising the steps of:
  (a) preparation of an inert core;
  (b) coating of the inert core with a suspension which comprises the benzimidazole compound of the formula I and at least one acidic reacting compound said suspension containing no alkaline compound and, having a pH in the range from about 6.5 to 6.95, in particular from 6.6 to 6.95;
  (c) application of at least one inert layer;
  (d) application of an enteric layer.

18. The process of claim 17 comprising the application of a first and second inert layer.

19. The process of claim 18, wherein the first inert layer is applied from a coating solution or suspension which has a pH in the range from about 6.5 to 6.95, in particular, in the range from 6.6 to 6.95.

20. The process of claim 17, wherein the layers are applied by means of a fluidized bed coating apparatus.

* * * * *